(12) United States Patent
Feldman et al.

(10) Patent No.: US 8,323,183 B2
(45) Date of Patent: Dec. 4, 2012

(54) FORWARD LOOKING OPTICAL COHERENCE TOMOGRAPHY ENDOSCOPE

(75) Inventors: Martin Feldman, Baton Rouge, LA (US); Dooyoung Hah, Baton Rouge, LA (US)

(73) Assignee: Board of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 198 days.

(21) Appl. No.: 12/444,703

(22) PCT Filed: Oct. 9, 2007

(86) PCT No.: PCT/US2007/080765
§ 371 (c)(1),
(2), (4) Date: May 5, 2009

(87) PCT Pub. No.: WO2008/045851
PCT Pub. Date: Apr. 17, 2008

(65) Prior Publication Data
US 2010/0049002 A1 Feb. 25, 2010

Related U.S. Application Data

(60) Provisional application No. 60/851,201, filed on Oct. 12, 2006.

(51) Int. Cl.
*A61B 1/06* (2006.01)
*G02B 26/08* (2006.01)
(52) U.S. Cl. ...... 600/182; 600/173; 600/160; 359/212.1
(58) Field of Classification Search ............... 359/212.1, 359/213, 214.1, 215.1, 205.1, 207.6; 348/203; 600/173, 160, 182, 425, 476; 250/227.26; 356/477, 479
See application file for complete search history.

(56) References Cited

U.S. PATENT DOCUMENTS 5,569,292 A * 10/1996 Scwemberger et al. ...... 606/185
(Continued)

FOREIGN PATENT DOCUMENTS

KR 10-2007-0082311 8/2007
(Continued)

OTHER PUBLICATIONS

Chong, C., "Optically modulated MEMS scanning endoscope," *IEEE Photonics Tech. Lett.*, vol. 18, pp. 133-135 (2006).
(Continued)

*Primary Examiner* — John P Leubecker
*Assistant Examiner* — Ronald D Colque
(74) *Attorney, Agent, or Firm* — John H. Runnels; Bonnie J. Davis

(57) ABSTRACT

A forward-looking, optical coherence tomography, endoscopic probe is disclosed capable of high resolution with a small diameter. Light is focused and scanned during three passes through a lens. A light source supplies light to the proximal side of the lens. The light makes a first pass through the lens, and is reflected from a fixed mirror on the distal side. The reflected light makes a second pass from the distal side to the proximal side, and exits the lens at the proximal side, and is reflected by a scanning mirror. The light makes a third pass through the lens from the proximal side to the distal side to a sample to be imaged. The light is focused during each of the three passes through the lens. Light reflected from the sample passes back through and is focused by the same system.

8 Claims, 11 Drawing Sheets

U.S. PATENT DOCUMENTS

| | | | | |
|---|---|---|---|---|
| 6,445,944 | B1* | 9/2002 | Ostrovsky | 600/425 |
| 7,252,634 | B2* | 8/2007 | Mizumo | 600/160 |
| 7,261,687 | B2* | 8/2007 | Yang | 600/173 |
| 2004/0097791 | A1* | 5/2004 | Tokuda et al. | 600/173 |
| 2004/0181148 | A1* | 9/2004 | Uchiyama et al. | 600/425 |
| 2005/0143664 | A1 | 6/2005 | Chen | 600/478 |

FOREIGN PATENT DOCUMENTS

WO PCT/US2006/037132 4/2006

OTHER PUBLICATIONS

Jung, W. et al., "Three-dimensional endoscopic optical coherence tomography by use of a two-axis microelectromechanical scanning mirror," *Appl. Phys. Lett.*, vol. 88, pp. 163901-1 through 163901-3 (2006).

Liu, X. et al., "Rapid-scanning forward-imaging miniature endoscope for real-time optical coherence tomography," *Optics*, vol. 29, pp. 1763-1765 (2004).

Wu, J. et al., "Paired-angle-rotation scanning optical coherence tomography forward-imaging probe," *Optics Letters*, vol. 31, pp. 1265-1267 (2006).

Xie, T. et al., "Endoscopic optical coherence tomography with new MEMS mirror," *Elect. Lett.*, vol. 39, pp. 1535-1536 (2003).

Xie, T. et al., "Fiber-optic-bundle-based optical coherence tomography," *Optics Letters*, vol. 30, pp. 1803-1805 (2005).

Xie, T. et al., "GRIN lens rod based probe for endoscopic spectral domain optical coherence tomography with fast dynamic focus tracking," *Optics Express*, vol. 14, pp. 3238-3246 (2006).

Yeow, J. et al., "Micromachined 2-D scanner for 3-D optical coherence tomography," *Sensors and Actuators* A, vol. 117, pp. 331-340 (2005).

* cited by examiner

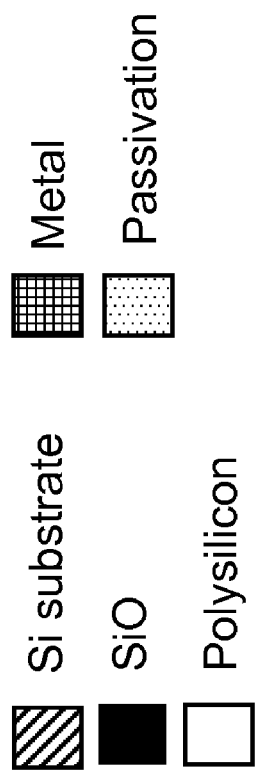
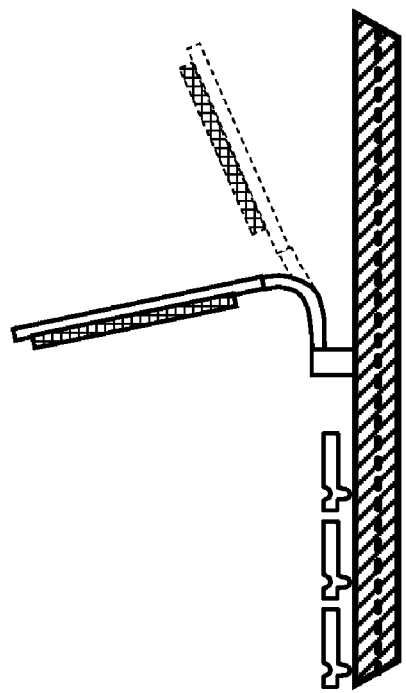
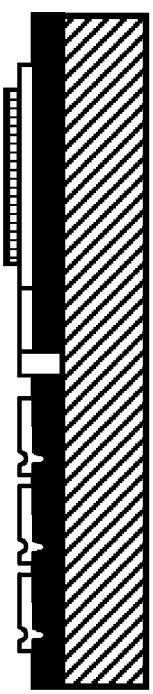
Fig. 7A
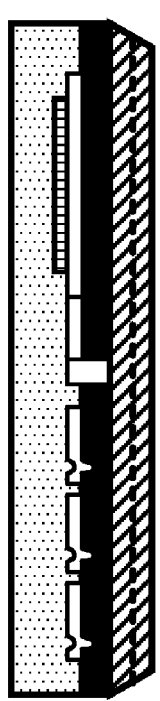
Fig. 7B
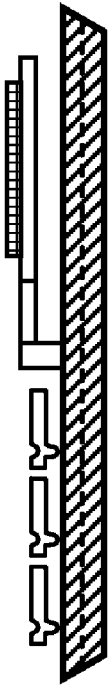
Fig. 7C
Fig. 7D

FORWARD LOOKING OPTICAL COHERENCE TOMOGRAPHY ENDOSCOPE

This is the United States national stage of international application PCT/US2007/080765, international filing date 09 Oct. 2007, which claims the benefit of the 12 Oct. 2006 filing date of U.S. provisional patent application Ser. No. 60/851,201 under 35 U.S.C. §119(e).

TECHNICAL FIELD

This invention pertains to endoscopy; particularly to a forward-looking, optical coherence tomography endoscope probe having a small outer diameter.

BACKGROUND ART

There is a continuing, unfilled need for improved endoscopic techniques, methods and apparatus to obtain optical images of tissue inside a patient, while minimizing the patient's discomfort and minimizing any damage caused by the imaging probe itself. In particular, there is an unfilled need for a forward-looking, optical coherence tomography endoscope probe having a small outer diameter. Existing probes are either side-firing, or if forward-looking have a large diameter or otherwise have an unduly complex construction.

One example of the many conditions for which there is a need for improved endoscopic techniques is gastric cancer. Gastric cancer is the fourth most common cancer and the second leading cause of cancer death in humans worldwide. About 90% of stomach tumors are adenocarcinomas, which are subdivided into two main histological types: 1) well-differentiated- or intestinal-type, and 2) undifferentiated- or diffuse-type. Recently, the incidence of intestinal-type tumors of the stomach has decreased, but the incidence of diffuse-type gastric carcinomas has increased. In general, countries with higher incidence rates of gastric cancer, such as Japan, have better survival rates than countries with lower incidence. Early-detection screening in high-risk areas has led to decreased mortality rates. When disease is confined to the inner lining of the stomach wall, 5-year survival is about 95%. Unfortunately, few gastric cancers are discovered at an early stage in the United States, leading to 5-year relative survival rates of less than 20%. Similarly, in European countries, the 5-year relative survival rates for gastric cancer vary from 10% to 20%. Hence, despite major research and clinical efforts, the number of deaths from gastric cancer has not decreased in recent years. A major clinical goal is early detection and surgical excision.

The prognosis for patients with suspected gastric cancer depends strongly on early detection and accurate preoperative staging. Other factors that influence prognosis are the depth of wall invasion, the presence or absence of lymph node metastases and distant metastases. Accurate preoperative evaluation at an early stage offers the best prognosis, and is essential for planning an optimal therapy, including an evaluation of the appropriateness of a limited surgery such as endoscopic mucosal resection or laparoscopic surgery. Although diagnostic advances in endoscopy techniques and double-contrast barium studies allow the detection of small lesions early in the course of the disease, the depth of tumor invasion cannot readily be determined by either of these methods. Currently, the preoperative staging of gastric cancer is usually diagnosed by computed tomography (CT). Continued refinement of CT techniques has improved the ability to stage gastric cancer. Nevertheless, results are still not satisfactory, especially for evaluating tumor depth. There is an unfilled need for improved methods to image and stage gastric tumors and other tumors.

Advances in CT scanners and computer technology have made more powerful and affordable 3D imaging systems available. To improve tumor staging by CT, it is essential to precisely locate the tumor. The detection of gastric cancer is influenced by factors including morphologic features, thickening of the gastric wall, and the degree of tumor enhancement. In a CT scan, a lesion is inferred to be cancerous when the gastric wall shows focal thickening, or when the gastric wall has an unusual contrast-enhancement pattern. The depth of tumor invasion on CT is usually classified according to a standard system. The detectability of early gastric cancers by CT is very low, with a rate of 20% to 53%. Accordingly, in most studies that have evaluated staging of gastric cancer, the absence of an abnormal finding on imaging is considered to be the earliest stage of cancer. With the introduction of techniques such as fast scanning, rapid infusion of intravenous contrast medium (dynamic CT scanning), and gastric water filing, the tumor detection rate has markedly increased, because two or three layers of enhanced gastric wall can be visualized. However, even with dynamic CT scanning, it is well known that gastric cancers located on the horizontally-oriented portion of the gastric wall are difficult to detect due to poor z-axis resolution and the partial volume averaging effect. In addition, using CT it is slightly easier to detect protruding early gastric cancers than flat, depressed, or excavated tumors. Although recent improvements in CT techniques have overcome some of the limitations of conventional axial CT, and while they allow improved tumor detection and localization, the detection of early gastric cancers in the absence of a thickened gastric wall remains difficult.

Optical coherence tomography (OCT) is an emerging branch of endoscopy. Optical coherence tomography (OCT) is an imaging technique that uses backscattered light to obtain cross-sectional images of tissue. It is analogous to ultrasound imaging, except that near-infrared light is used rather than sound, and the signal is generated at optical discontinuities rather than acoustic discontinuities. Conventional OCT is an outstanding technique for imaging superficial tissue. It can be used to obtain in vivo cross-sectional or even volume images within body cavities and tissues. OCT typically has a resolution of 5-20 µm, and a depth of penetration of 1-2 mm. The axial resolution, along the line of sight, is determined by the light source and detection electronics. This has historically tended to be comparable to the transverse resolution, which is determined by the optical system. OCT lacks cellular resolution but is able to visualize subsurface structures associated with early stage cancers and other diseases, such as epithelial thickening and abnormal glands. OCT has been used to image a variety of tissues that can be accessed either directly or via endoscope or catheter. For instance, pilot studies have indicated that OCT can detect early neoplastic changes in the colon, skin, and esophagus, and thin-capped fibroatheroma. OCT has been used to image pathologies of the retina.

OCT has been used for in vivo endoscopic imaging of human stomach. It has been used to image glandular epithelium, muscularis mucosa, submucosa, and muscularis propria, gastric pits, and highly reflective lamina propria. Optical coherence tomography systems may be used, for example, in studying the microvasculature, skin, tendon, ovary, and colon of animal models and human patients. It has been reported that OCT images are superior to those from ultrasound in visualizing superficial layers of the stomach. Doppler OCT, a variant sensitive to Doppler shifts caused by moving blood cells, has been used to image pathologies of the gastrointestinal tract, variations in tissue structure, and blood vessel anatomy. To our knowledge, no prior OCT imaging has successfully visualized gastric submucosa.

Micro-electro-mechanical systems or MEMS employ devices or systems built using microfabrication processes similar to those used to fabricate integrated circuits (ICs). Many MEMS devices have entered into mass production and have established markets. However, MEMS is still a young technology, especially in the biomedical applications.

In a graded index lens ("GRIN lens") the index of refraction changes as a function of position. Most GRIN lenses are cylindrical rods in which the index of refraction decreases with distance from the axis. For example, one GRIN lens that may be used in the present invention is a commercially available lens 1 mm in diameter, whose refractive index, n, is a parabolic function of the radial distance, r, from the cylindrical axis:

$$n(r) = n_0\left(1 - \frac{A}{2}r^2\right)$$

For a commercially-available lens that we used in a model of the present invention (NSG Europe, Temse, Belgium), in the above equation $A=0.3564$ and $n_o=1.5916$ (the index of refraction on-axis.) Much of the focusing takes place within the body of the GRIN lens. In a GRIN lens with a parabolically-varying index of refraction, it can be shown that a ray of light follows a sinusoidal path in the lens. GRIN lenses are often sold in lengths that correspond to the number of oscillations of this sine wave. For example, a ray in a lens of length "$2\pi$" will undergo one complete oscillation of the sine wave, and a lens of length "$\pi/2$" will undergo one quarter of an oscillation, or 90° of oscillation. FIG. 1 depicts a ray trace for two beams with $NA=0.12$ through a "$\pi/2$" lens. Both beams enter the lens parallel to the axis, one at a radius $r=0$, and the other at $r=0.4$ mm. The rays in the beams follow sinusoidal paths. At the length $\pi/2$ (2.63 mm) both beams are centered on the axis of the lens, and the spread of both lies within $\pm 0.134$ mm of the axis. At the length $\pi/2$, the rays from a given beam are all parallel to one another (although the direction of the rays will, in general, differ from the direction of rays from a different starting beam). The length $\pi/2$ corresponds roughly to a conventional lens plus a focal distance, since a point source at one end is transformed into a parallel beam at the other (and vice versa).

A GRIN lens of length "$\pi/2$" may also be used to image objects located outside the lens. FIG. 2 depicts an example of 1:1 imaging with a $\pi/2$ lens, with an object point and an image point each spaced 1.57 mm from opposite sides of the GRIN lens. In this example the index of refraction on either side of the lens is 1.5, approximately the average of the varying index within the lens. The sinusoidal paths shown inside the lens are parallel at its midpoint ($\pi/4$), and they converge symmetrically to the object and image points.

There are two principal types of OCT endoscopes: forward-looking, and side-scanning. A side-scanning endoscope is useful to examine tubular organs. A forward-looking endoscope can be used to image a hollow organ or a tissue that has at least one wall that is perpendicular, or nearly perpendicular, to the axis of the scope. Forward-looking endoscopes have the advantage that they can look ahead and collect data before entering and possibly damaging the tissue. Transverse scanning in OCT endoscopes has been conducted by rotating the entire fiber-optic assembly with an external motor, and also by scanning a mirror with an internal galvanometric motor. In prior forward-looking endoscopes the mechanisms used to scan have either required relatively wide probes, or the design of the probes makes them prone to vibration, neither of which is desirable. The forward-looking endoscopes that have been reported to date are typically a few mm in diameter. Reducing the diameter of the probe can help minimize tissue damage, but to our knowledge the narrowest forward looking probes reported previously have been about 1.65 mm in diameter. It would be desirable to reduce the diameter to 1.5 mm, 1.25 mm, 1 mm or even smaller, but such a small diameter is difficult to achieve with existing designs.

Some OCT endoscopes have been built using MEMS technology, both for side-scanning and forward-looking OCT. The reported devices have used either electrostatic actuators or electro-thermal actuators. Reported probes to date have shown an axial resolution of 4~13 µm, a transverse resolution of 13~35 µm, and an imaging speed of 5~20 frame/sec with either 2- or 3-dimensional imaging capability. However, the outside diameter of these probes has usually been in the range of 4 to 6 mm, though some are smaller. There is an unfilled need for further miniaturization of such optical probes, preferably with a diameter ~1.5 mm or smaller, to penetrate through small body cavities and to minimize damage to tissues.

A scanning mechanism is required to have a useful OCT probe. Yet, a scanning mechanism tends to increase the diameter of the probe, which is undesirable, or it results in a sideways-looking probe rather than a forward-looking probe. Placing a mirror in line with a GRIN lens at a 45° angle preserves the small diameter of the probe, but results in a sideways-looking probe. While a side view can be helpful in some situations, a forward-looking probe is more generally useful. Other types of forward-looking probes that have been reported include one in which a distal scanning mirror is placed alongside a GRIN lens, which approximately doubles the diameter of the probe; and one in which a complex counter-rotation system with two GRIN lenses is employed, which is mechanically complex, rigid, and may be prone to vibration.

Side-firing endoscopes are disclosed, for example, in W. Jung et al., "Three-dimensional endoscopic optical coherence tomography by use of a two-axis microelectromechanical scanning mirror," *Appl. Phys. Lett.*, vol. 88, pp. 163901-1 through -3 (2006); C. Chong, "Optically modulated MEMS scanning endoscope," *IEEE Photonics Tech. Lett., vol.* 18, pp. 133-135 (2006); and J. Yeow et al., "Micromachined 2-D scanner for 3-D optical coherence tomography," *Sensors and Actuators A*, vol.117, pp. 331-340 (2005).

J. Wu et al., "Paired-angle-rotation scanning optical coherence tomography forward-imaging probe," *Optics Letters*, vol. 31, pp. 1265-1267 (2006) discloses a forward-scanning OCT system that uses a pair of rotating, angled, gradient-index lenses to scan the output probe beam. A prototype probe was reported with an outer diameter of 1.65 mm, with the two lenses rotating at equal and opposite angular speeds of ~21 rpm. Because lenses with relatively high masses rotate rapidly through 360 degrees, as opposed to scanning through relatively smaller angles with a relatively low-mass mirror, this probe may be prone to undesirable vibrations and may, perhaps, be less reliable mechanically as compared to designs based on lower-mass scanning mirrors. The probe must presumably be rigid to accommodate this design.

T. Xie et al., "Endoscopic optical coherence tomography with new MEMS mirror," *Elect. Lett., vol.* 39, pp. 1535-1536 (2003) discloses a forward-scanning OCT probe in which a MEMS scanning mirror is positioned more-or-less adjacent to a GRIN lens. The outer diameter of the probe was 4.3 mm.

From the design depicted in FIG. 1 of that paper, it can be seen that the diameter will necessarily be substantially greater than that of the lens alone, since the probe must accommodate the lens and the mirror side-by-side.

X. Liu et al., "Rapid-scanning forward-imaging miniature endoscope for real-time optical coherence tomography," *Optics*, vol. 29, pp. 1763-1765 (2004) discloses a forward-scanning OCT probe having an outer diameter of 2.4 mm. Scanning was achieved by coupling a fiber-optic cantilever, positioned behind a GRIN lens, to a vibrating actuator. The design of the probe makes it inherently prone to vibration, and may make it difficult to implement three-dimensional scanning.

T. Xie et al., "GRIN lens rod based probe for endoscopic spectral domain optical coherence tomography with fast dynamic focus tracking," *Optics Express*, vol. 14, pp. 3238-3246 (2006) discloses forward-scanning and side-firing OCT probes based on gradient index lenses. Light from a single-mode fiber was steered by a servo mirror on the proximal end of the GRIN lens to perform a lateral scan on the entrance plane of the GRIN lens rod. The focal depth was varied dynamically without moving the probe, from a depth of 0 to 7.5 mm. The lateral scanning range was reported to be up to 2.7 or 4.5 mm, as determined by the diameter of the GRIN lens rod itself. This type of endoscope is rigid, limiting usefulness for gastric (and other types of) imaging. See also T. Xie et al., "Fiber-optic-bundle-based optical coherence tomography," *Optics Letters*, vol. 30, pp.1803-1805 (2005).

DISCLOSURE OF THE INVENTION

We have discovered a forward-looking, optical coherence tomography, endoscopic probe capable of high resolution with a small diameter, for example, 2 mm, 1.75 mm, 1.5 mm, 1.25 mm, 1 mm or smaller. Images may be two-dimensional (slices) or three-dimensional (volume). As illustrated schematically in FIG. 3, light is focused and scanned during three passes through a lens. A light source, preferably an optical fiber, supplies light near one edge of the proximal side of the lens, preferably a GRIN lens. The light makes a first pass through the lens from the proximal side to the distal side, and is reflected from a fixed mirror (e.g., silvered surface) on the distal side of the lens. The reflected light then makes a second pass through the lens from the distal side to the proximal side, and exits the lens at the proximal side, preferably as a parallel beam, and is then reflected by an external scanning mirror, preferably a MEMS device. The scanned, reflected light then makes a third pass through the lens from the proximal side to the distal side, and passes to a sample to be imaged. The light is focused onto an image plane, which may for example be on the surface of or in the interior of the sample. Light reflected from the sample passes back through the same system, and is focused on and collected by the optical fiber. The light collected by the fiber is used to construct a high-quality image, using techniques otherwise known in the art to deconvolve and construct two-dimensional or three-dimensional images, for example by analyzing interference with a reference beam in a Michelson-type interferometer. External vibration of the probe is minimal. The probe can be adapted for flexible or rigid applications.

BRIEF DESCRIPTION OF THE DRAWINGS

FIGS. 7(a) through 7(d) depict schematically the fabrication process flow for the MEMS scanning mirror chip.

MODES FOR CARRYING OUT THE INVENTION

Figure 1:
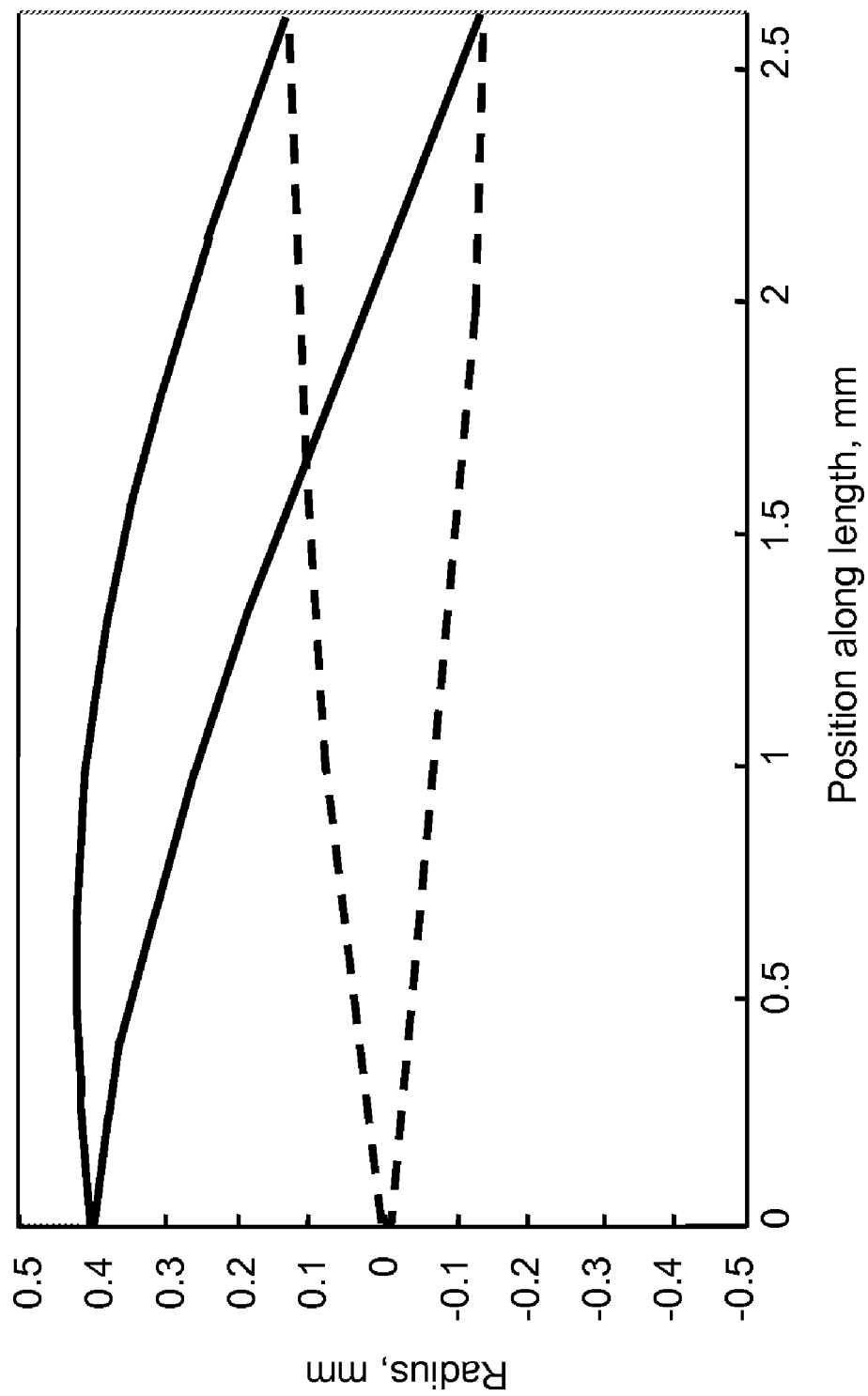
FIG. 1 depicts the outer rays of two beams with NA=0.12 entering a GRIN lens parallel to the axis.

The optical system must be compact. In a preferred embodiment, the system employs the remarkable imaging properties of GRIN lenses. GRIN lenses are commercially available, and are preferred because they are available in compact size and cylindrical shape, making them well-adapted for use in the present invention. Previous workers have also used GRIN lenses in other OCT endoscopes. Conventional lenses, while not preferred, may also be used.

The lightweight scanning mirror is placed in "back" of the lens (on the proximal side), allowing light to make a total of three passes through the lens, and allowing the outer diameter of the probe to be about the same as the diameter of the lens itself or slightly larger. Because the scanning mirror is behind the lens rather than to its side, forward scanning may be achieved without increasing the diameter of the probe beyond what is needed to accommodate the lens.

The scanning mirror may be fabricated using techniques known in the art, for example, by a commercial MEMS foundry. Etching processes known in the art may be used to separate chips, to size them to fit into the probe shell, and to remove sacrificial layers to release the moving components. Scratch drive actuators, similar to so-called inchworms, are incorporated into the chip to lift the mirror into operational position, and to provide the scanning motion. In a preferred embodiment, micro-scanners are fabricated by a combination of surface micromachining and bulk micromachining. The former uses multiple thin film layers to generate mechanical structures and to remove sacrificial materials. The thin film layers are patterned and etched in essentially the same way that integrated circuits are fabricated. However, later steps, when structures are released by etching sacrificial layers and become movable, differ from IC fabrication. An advantage of surface micromachining is that it can produce relatively complicated mechanical devices such as hinges, inchworm motors, levers, etc. In bulk micromachining the substrate itself is processed using wet or dry etching In assembling the probe, the small size of the components makes alignment in a relatively rugged package important. Micropositioners are used to align the components under a low power optical microscope. Fixtures hold them in place while they are permanently attached, for example with UV-curing epoxy.

Where desired, the performance of an endoscopic probe may be tested for optical resolution, focal length, depth of focus, flatness of field, response time, linearity, range of scan, etc. It will often be convenient to conduct preliminary tests with visible laser light, e.g., at 0.633 µm, followed by more extensive tests at the operating wavelength in the near IR, e.g., 1.3 µm.

The prototype endoscope is integrated into an existing OCT system for in vivo testing. The performance of the integrated system is tested by standards and demonstrated in vivo in rats, before being tested in humans in accordance with applicable statutes and regulations.

EXAMPLE 1

A simulation of the optical system was first conducted with large scale components. The distributed focusing of a $\pi/4$ GRIN lens was approximated with a series of three equally-spaced conventional lenses. A HeNe laser beam at a wavelength of 0.633 µm was focused by a microscope objective to a numerical aperture of 0.12 at the entrance to the lens, approximately the same numerical aperture as that for light entering the GRIN lens in the system depicted in FIG. 3. The laser light then made three passes through the lenses and was reflected from the mirrors as shown, before coming to a sharp focus downstream from the lens. This experiment demonstrated in principle the successful use of the novel optical system.

EXAMPLE 2

Figure 4:
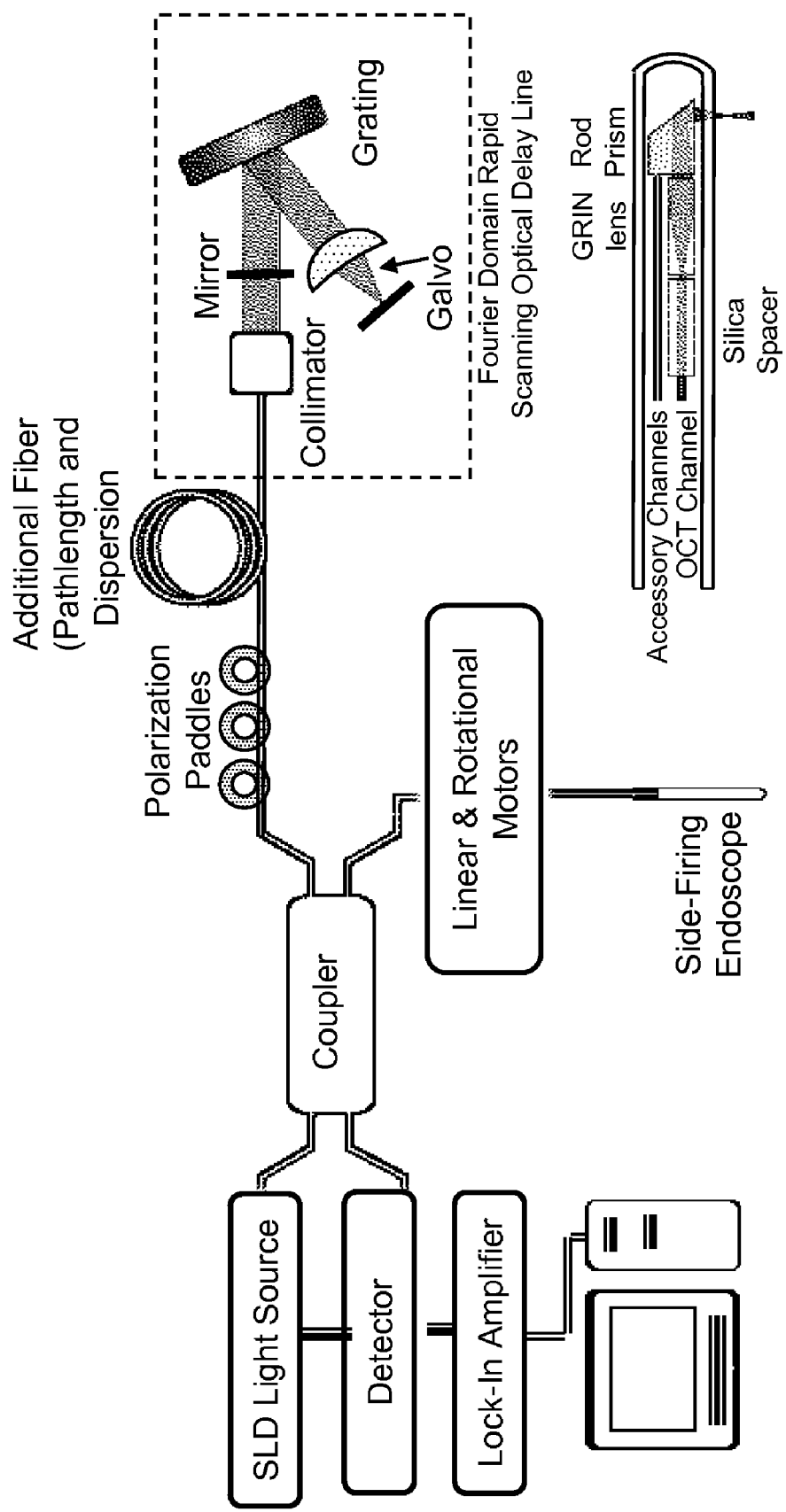
FIG. 4 depicts schematically a side-viewing endoscope OCT system.

FIG. 4 depicts a side-viewing endoscope OCT system for comparison. In many respects, except for those features of the new system that are novel, the new system may be operated in a generally similar manner to that used for a side-viewing endoscope OCT system. There is a superluminescent light source having a center wavelength of 1300 nm and a 100 nm bandwidth (Superlum D1300-HP, Moscow, Russia), for a coherence length on the order of 10 µm. A center wavelength of 1300 nm was chosen because of the ready availability of photonics components, and because tissue attenuation at that wavelength is low, allowing relatively deep imaging. Light from the source is split by a fiber-based Michelson interferometer into two paths: one path travels to the sample arm, where light is focused onto tissue or other sample; and one path travels to a reference arm, which includes a Fourier-domain, rapid-scanning optical delay line to modulate the optical path length. A relatively low coherence length is preferred, to maximize the resolution of signals from different depths within the sample. When the optical path lengths of light backscattered from the sample and light from the reference arm are the same, to within a distance of approximately the coherence length, then interference will be observed. By moving the position of a reference mirror (external to the probe), the length of the reference path varies, and backscattered light from various depths within the sample is observed via interference at corresponding path lengths. Thus different depths may be imaged without necessarily moving the probe, typically at depths up to a few millimeters, with a transverse (side-to-side) range of about 0.75-1.0 mm. Axial resolution is limited primarily by the coherence length, and transverse resolution is limited primarily by the numerical aperture of the lens. The prototype setup is capable of producing A-scans (image columns) at rates from about 100 to about 1000 A-scans/sec. Therefore, depending on the number of A-scans per image, images are acquired at rates between several images/second to several seconds/image. The interferometric signal is detected using a photodiode, and is demodulated using a multichannel filter and logarithmic amplifying circuitry. The data is acquired and processed using custom C# software with a high-speed data acquisition board. The axial resolution of this system is approximately 7 µm in tissue (or 10 µm in air).

The sample arm of the interferometer is a miniature endoscope containing one OCT channel (a single mode fiber) and three accessory channels (200 µm, multimode fibers). The accessory channels may be used for other functions, e.g., the insertion of an aiming beam, laser-induced fluorescence measurements, etc. Light in the OCT channel is focused using a SELFOC™ GRIN lens to produce a lateral resolution of 20 µm at a working distance of 400 µm from the endoscopic window. This endoscope is side-firing, using a rod prism to direct light from the side of the endoscope window. The endoscopic optics are housed within a 2-mm outer diameter, 40-mm long quartz optical window. Two stepper motors are used to rotate and translate the optics within the optical window, to vary the position at which the image is taken. The motion is transferred to the optics using an inner polyimide tubing, while the endoscopic window remains fixed in the outer sheath of the endoscope. This side-firing endoscope is well-suited for imaging tubular structures, and has been used, for example, in imaging mouse colon. However, it is less than ideal in other applications, such as imaging inside large hollow organs, guiding biopsy needles, and other circumstances where a forward-looking endoscope would be more appropriate.

EXAMPLE 3

To demonstrate the feasibility in principle of imaging the interior of a rat stomach through OCT, a side-firing OCT system was used to image excised specimens. The stomachs of three rats were excised, opened, rinsed with saline, and pinned flat to a wax block. The light source used was an 890 nm superluminescent diode. The OCT system had a resolution of approximately 8 µm. Images 1 mm deep by 6 mm lateral were successfully taken. The OCT system easily imaged through the thin (250-300 µm) layers of the stomach, and all major layers could be identified. Blood vessels were also visible. This preliminary study demonstrated that OCT can perform imaging that would be useful, for example, in diagnosing gastric cancer. To enhance in vivo image quality, it is preferred to place the animals (or patients) on a liquid diet (e.g., Pedialyte™) for ~12 hours before imaging, to reduce solids content in the stomach.

EXAMPLE 4

Small Diameter Optical System

Figure 2:
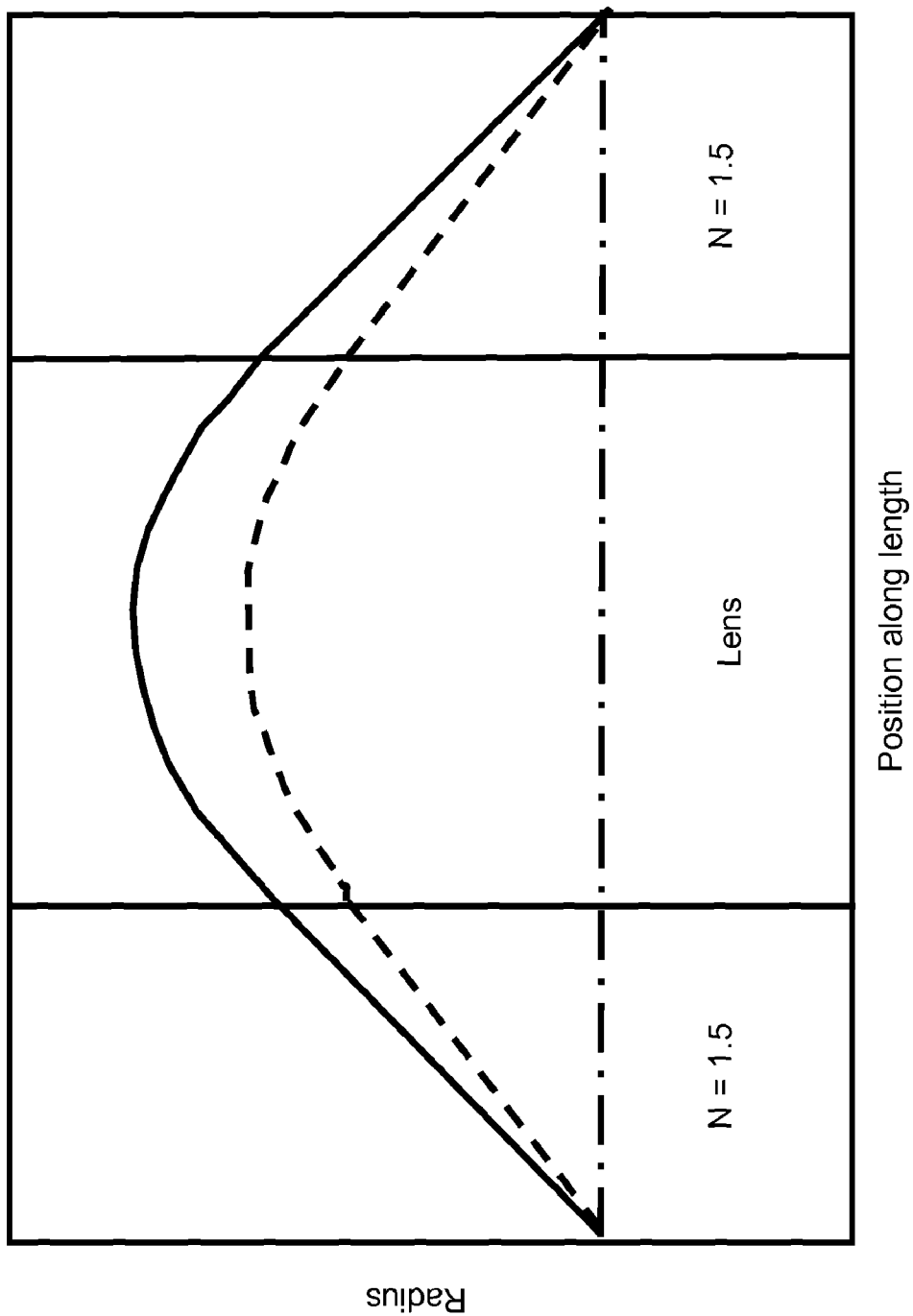
FIG. 2 depicts an example of 1:1 imaging with a $\pi/2$ GRIN lens
Figure 3:
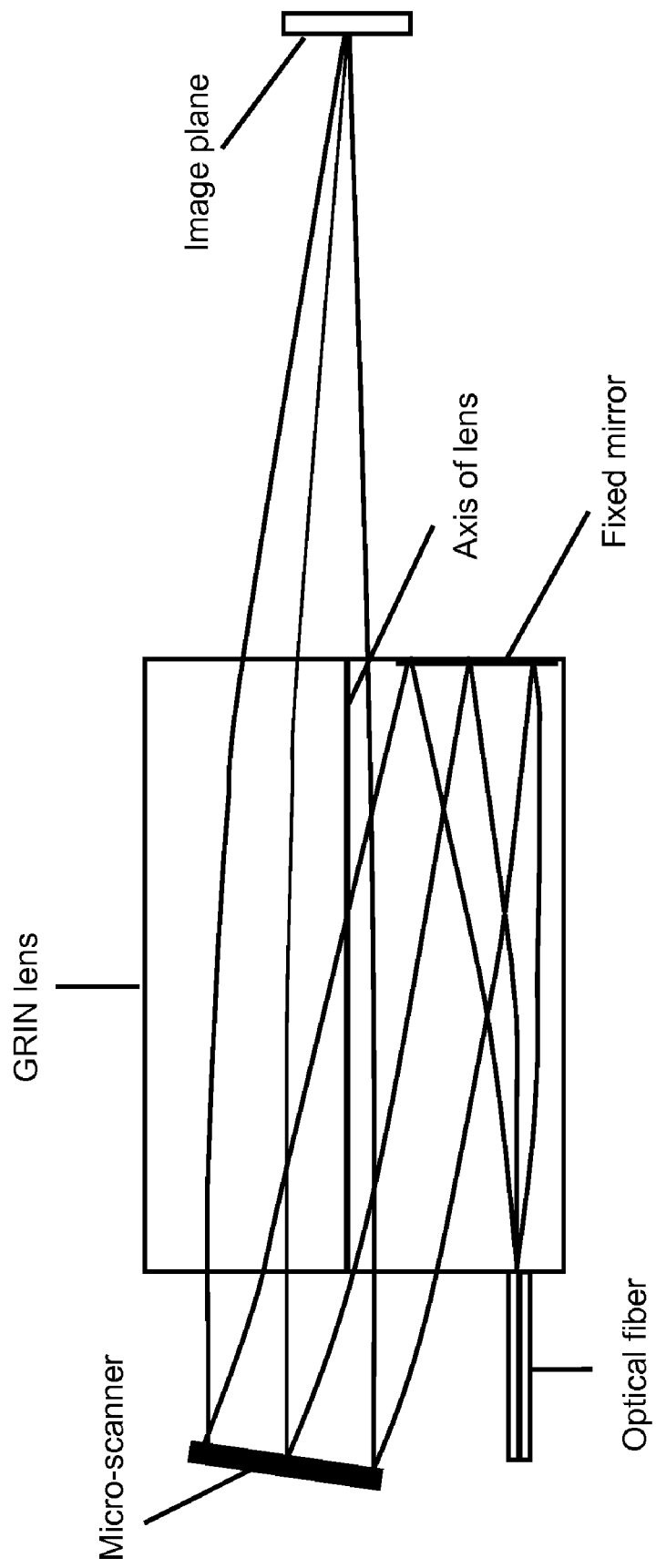
FIG. 3 illustrates schematically the optical system used in one embodiment of this invention.

Conceptually, the ray paths depicted in FIGS. 1 and 2 are combined in a compact imaging system, as shown schematically in FIG. 3. The lens of radius 0.5 mm (1.0 mm diameter) has a length of "$\pi/4$" (1.315 mm). Light enters the lens through an optical fiber, which is bonded to the lens with optical cement at a distance of 0.4 mm from the cylindrical axis. A preferred wavelength is 1.3 µm, and a preferred optical NA for the fiber is 0.12. The light expands as it travels through the lens from the fiber on the proximal end towards the fixed mirror on the distal end. The fixed mirror on the distal side of the lens is made by depositing an aluminum layer through means known in the art. The rays reflect from the mirror, and then pass through the lens on the proximal end, offset as shown. The rays in a parallel beam then strike the scanning mirror outside the lens.

After reflecting from the scanning mirror the light reenters the proximal side of the lens, still as a parallel beam, but at an angle that depends upon the angle of the scanning mirror. The light converges as it passes through the lens a third time, finally coming to a focus in the image plane as shown. If the intervening material has an index of refraction of 1.5, then the image plane in this prototype is about 1.57 mm from the distal side of the lens.

Since the light both reflects from and passes through the distal side of the lens, only a portion of that surface is mirrored. It is preferred that the angle of the scanning mirror is such that the light it reflects does not substantially intersect either the mirrored portion of the distal lens surface, nor the lateral side of the lens, nor the lateral side of the spacer.

Figure 5:
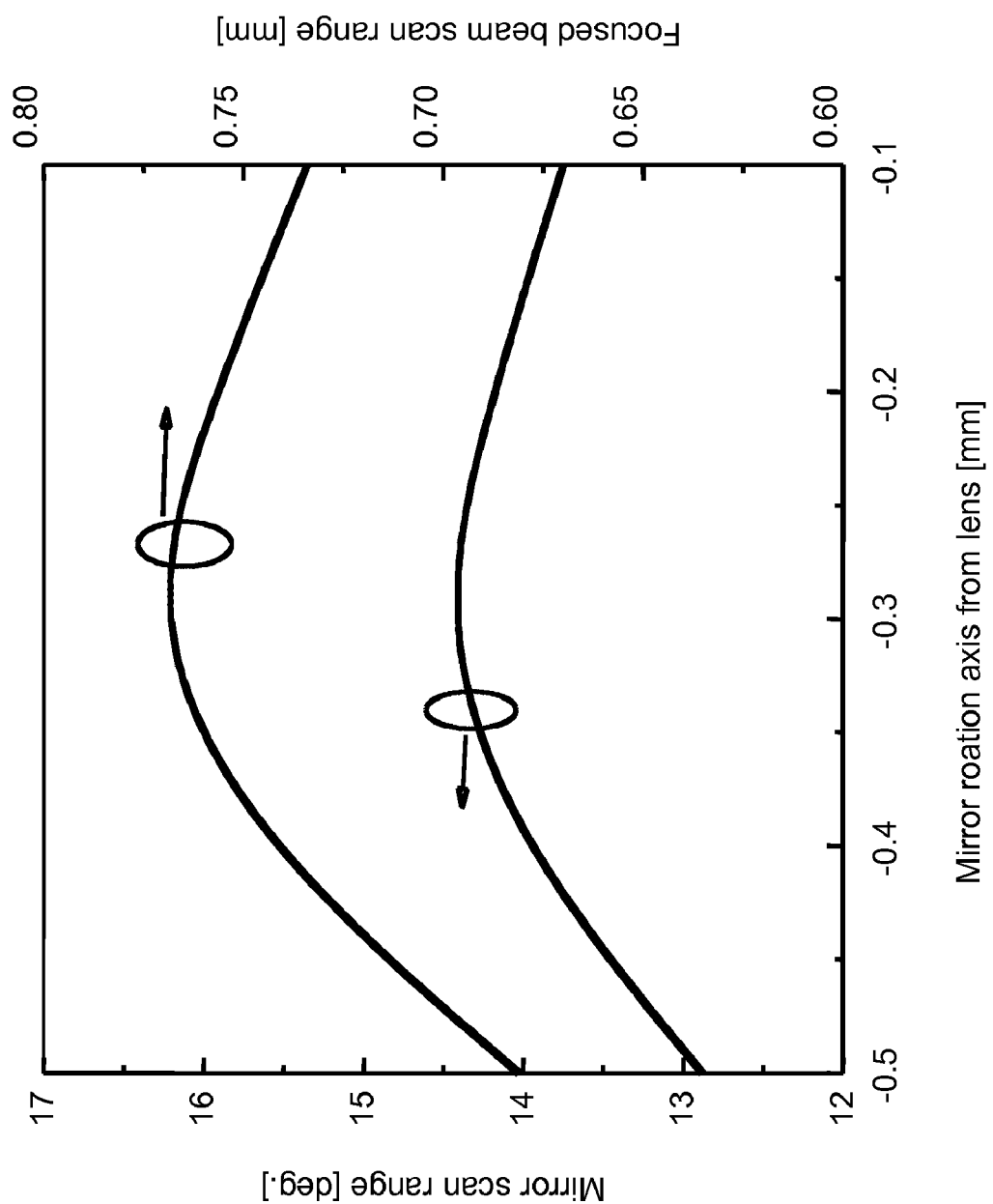
FIG. 5 depicts the scanning ranges of the mirror and of the focused beam as a function of the distance between the axis of rotation of the mirror and the lens.

The usable angular range for the scanning mirror in the prototype system is about 14 degrees, which occurs when the mirror is spaced about 0.3 mm from the lens. See FIG. 5, which depicts scanning ranges for the mirror and for the focused beam as a function of the distance between the axis of rotation of the mirror and the lens. The resulting scan of the focused spot moves through a distance of about 0.75 mm long, and extends almost to the edge of the spacer. The NA remains constant throughout the optical path. For a diffraction-limited lens, the focused spot size and the depth of focus are given by $$\text{Spot size} \approx \frac{\text{wavelength}}{2NA} = 5.4 \, \mu m$$

$$\text{Depth of focus} \approx \frac{\text{wavelength}}{2NA^2} = 45 \, \mu m$$

The GRIN lenses are used as received from the manufacturer. Experience has shown that the manufacturer's control of lens length is not precise, so lenses are measured and selected for the proper length. The effect of a small length variation is to change the image plane slightly, with corresponding changes in the length of scan and the focused spot size. Probes made with varying lengths of the lens will produce image planes at different distances from the lens. Aluminum of thickness 100 to 200 nm is deposited on one end of a GRIN lens. The lens is secured in a 1 mm inner diameter stainless steel shell, coated with resist, and patterned to form the reflecting mirror across part of the distal surface. The lens and a 0.12 NA fiber, matching available 1.3 μm lasers, are mounted in a micropositioner. A small amount of UV-curing optical cement is applied to the end of the fiber, the fiber is brought into contact with the required portion of the front surface of the lens, and the cement is cured in place.

EXAMPLE 5

Small-Dimension Micro-Scanner Chip Made Using MEMS Technology

It is preferred for the MEMS chip to be inserted parallel to the optical axis, within a stainless steel tube, and for the scanning mirror to be folded up, out-of-plane, preferably ~74°. This arrangement has two significant advantages over placing the MEMS chip perpendicular to the optical axis, and using an in-plane scanning mirror. First, the required alignment tolerance between the scanning mirror and rest of the optical system may be relaxed, because the scanning mirror's folding angle can be fine-tuned even after assembly of all the components has been completed. Second, electrical wires can easily access the front surface of the MEMS chip, eliminating the need for via-holes through the wafer.

Several folding mechanisms are currently available in MEMS technology. Preferred is electromechanical assembly control using microactuators such as scratch drive actuators (SDA) with spring latches. This technique should outperform alternative methods such as surface-energy-driven material reformation, or thermal-stress-induced cantilever deformation, in at least three respects: the ability to have a large folding angle, the ability to precisely control the angle, and the ability to fine-tune the conformation after assembly of the components. SDA is an inchworm-like electrostatic actuator that moves forward by a step whose size is determined by the geometry and by the level of the voltage pulse. In operation, the scanning mirror pivots on hinges, and is rotated upwards by SDAs. Its steady-state angular position is then maintained by spring latches (FIG. 6).

The SDAs are also used for scanning the mirror. One way to accomplish bidirectional scanning is to place a second set of SDAs, facing a direction opposite to that of the first set. The precision and the accuracy of the mirror scan angle are affected by factors including the magnitude and uniformity of the SDA stroke. Other factors affecting precision and accuracy include the shape, number, and size of the bushings, and the dimensions of the plates. A single SDA stroke is typically on the order of tens of nanometers, corresponding to an angular step of a few millidegrees. SDAs typically have a speed of about 1 cm/s, corresponding to a mirror scanning frequency of about 180 Hz for a 14° range of mirror rotation.

Figure 6:
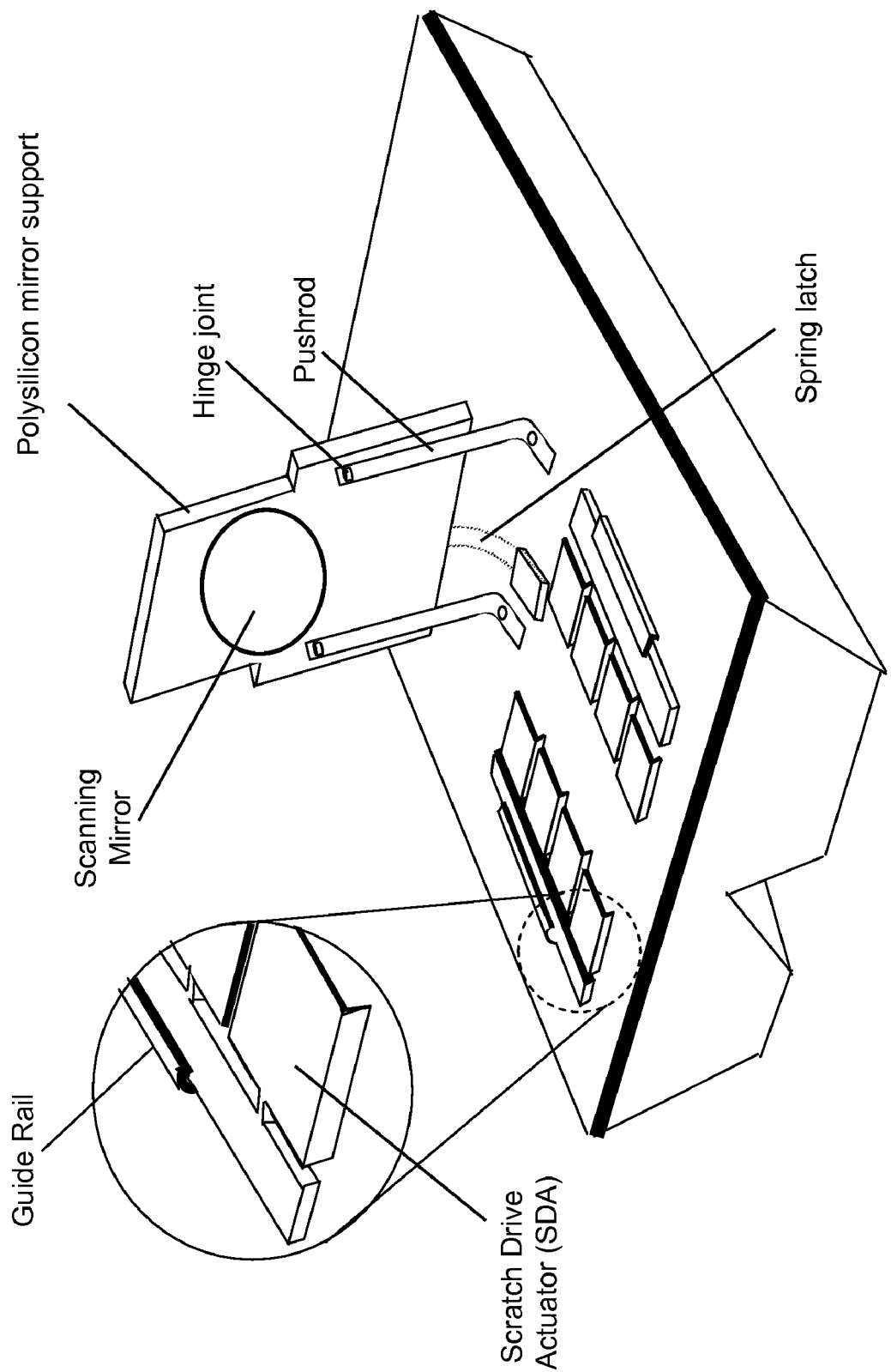
FIG. 6 depicts schematically the scanning micromirror with scratch drive actuators.

The embodiment depicted in FIG. 6 is designed to perform one-axis scanning, and hence is capable of cross-sectional imaging. This embodiment may readily be modified using to form a two-axis scanner, by adding extra hinge joints on the mirror supports, to provide volumetric images.

The MEMS chips, including scanning mirror, mechanical assembly components (hinges, spring latches, pushrods), and SDAs are manufactured using MEMS manufacturing techniques otherwise known in the art, for example by a commercial foundry service. Two structural polysilicon layers are used for all moving parts, two sacrificial oxide layers for device release, and a metal layer is used for a reflecting surface and bonding pads. The MEMS chips are thinned to fit within a stainless steel shell. KOH (potassium hydroxide) or TMAH (tetramethylammonium hydroxide) anisotropic etching follows the double-side lithography to separate the dies, and to leave slanted side walls, with a trench on the bottom through which the fiber passes. The front surface is passivated and remains unetched. The moving parts are released by etching a sacrificial oxide layer in HF, and the dies are placed into a supercritical $CO_2$ dryer for stiction-free drying. Thin contact wires are bonded to pads on the substrate. Finally, the scanning mirror is folded up by applying voltage pulses to the SDAs. FIGS. 7(a) through 7(d) depict schematically the fabrication process flow for the MEMS chip. FIG. 7(a) depicts fabrication. FIG. 7(b) depicts substrate thinning and silicon anisotropic etching. FIG. 7(c) depicts device release in HF and supercritical drying. FIG. 7(d) depicts assembly of the scanning mirror with SDAs. The components in FIGS. 7(a)-7(d) (and in the other figures in general) are not necessarily drawn to scale. For clarity, hinge parts are not depicted.

EXAMPLE 6

Incorporation of the Optical System and Scanning Mirror, and Testing.

Figure 8B:
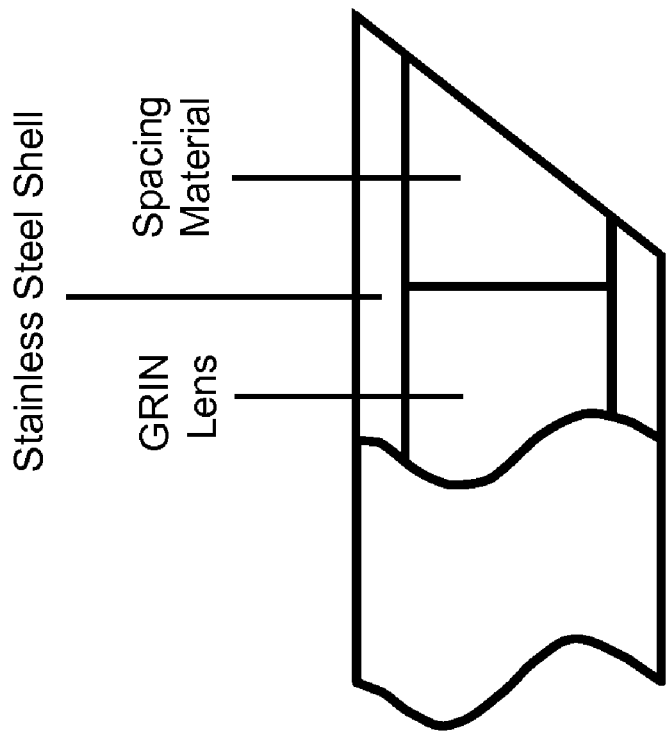
FIGS. 8(a) and 8(b) depict schematically cross-sectional views of blunt and sharp endoscopic probes, respectively, used in different embodiments of the invention.
Figure 8A:
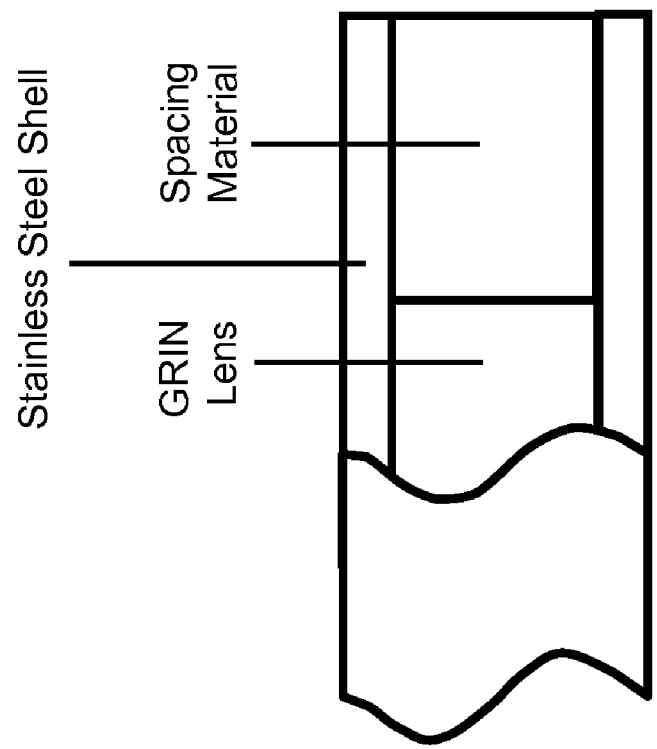
Figure 9A:
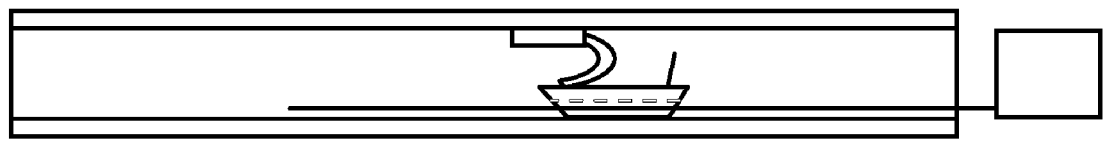
FIGS. 9(a) through 9(d) depict schematically the construction of a sharp probe used in an embodiment of this invention.
Figure 9B:
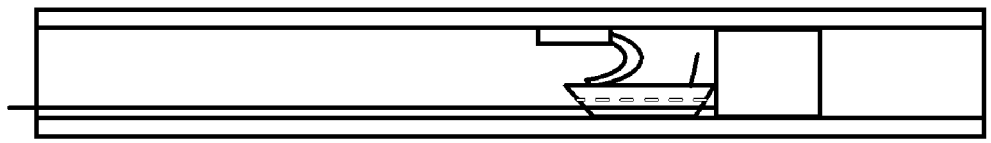
Figure 9C:
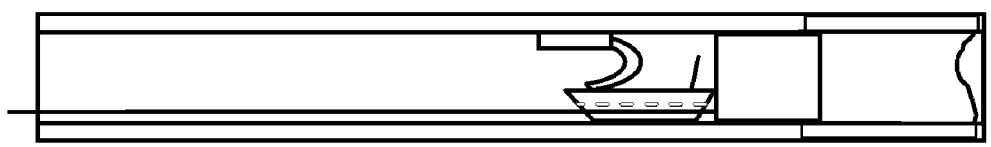
Figure 9D:
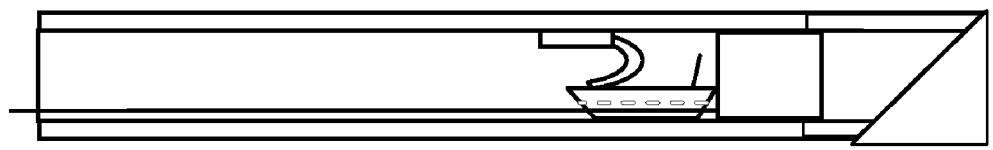
Figure 10A:
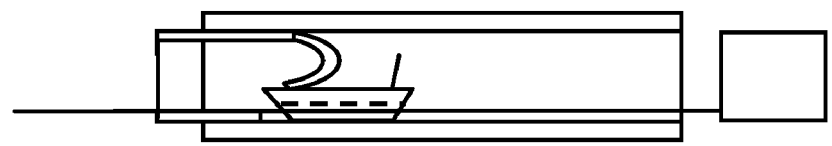
FIGS. 10(a) through 10(d) depict schematically the construction of a blunt probe used in an embodiment of this invention.
Figure 10B:
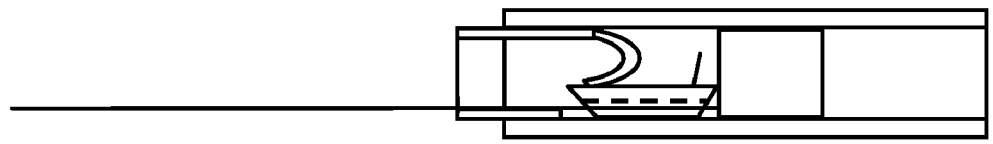
Figure 10C:
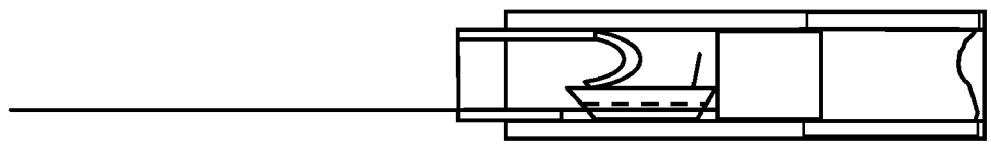
Figure 10D:

Both blunt (FIG. 8(a)) and sharp (FIG. 8(b)) probes are manufactured and tested. In a blunt probe the spacing material ends in a polished surface perpendicular to the axis of the probe. (The function of the spacing material is to allow an appropriate distance between the distal end of the lens and the focal plane that is to be imaged. Also, it is preferred that the lens itself should not come into contact with tissue.) The focal plane lies just outside the probe. A blunt probe is useful for exploring body cavities, where the ability to bring the probe close to, or even to push up against, the inner surface of the cavity is important. A sharp probe is useful where it is necessary to penetrate through tissue. The probe is attached to a relatively long flexible umbilical lead carrying electrical and optical connections.

EXAMPLE 7

Manufacture of Sharp Probe

In a sharp probe the spacing material ends in a polished surface cut, at a 45° angle (for example) to the axis of the probe. A sharp probe is useful for inserting into tissue. The focal plane will lie near the sharp leading edge of the probe, with imaging through about an additional half millimeter of tissue or body fluids. Optionally, an additional channel could be added to the probe to flood the region in front of the probe with saline or other solution. However, the advantages of maintaining the diameter of the probe at 1.25 mm or below may outweigh the disadvantages from the small amount of signal degradation produced by omitting a saline or other fluid source. The oblique surface of the sharp probe changes the incidence angle of the focused light (by a few degrees) and tilts the focal plane (by a few tens of microns). These are relatively small effects that may be neglected or compensated as desired. The sharp probe is preferably relatively short, and is preferably rigidly attached to a handle.

The construction of a sharp probe is illustrated schematically in FIGS. 9(a) through (d) (not to scale). The mirror assembly is loaded at a predetermined position within stainless steel tubing, which has an inside diameter slightly greater than 1 mm. (FIG. 9(a)) The fixture includes a spring clip to position the mirror assembly against one side of the tube, and an open area to allow the passage of control wires and the fiber. The tube is ~7 to 10 cm inches long. A fiber attached to the GRIN lens is threaded through the stainless steel tubing, and through the open area in the mounting fixture, until the lens comes to a stop against the substrate of the mirror assembly. (FIG. 9(b)) A very small amount of epoxy, placed on the fiber near the lens, is carried under the mirror assembly, and bonds it to the stainless steel tube. When the epoxy has hardened, the mounting fixture is removed. UV-curing epoxy is added to the tube, covering the lens from the back side to the top of the tube. (FIG. 9(c)). The tube is cut for a focal length of 1.57 mm past the distal end of the lens at a 45° angle, and the cured UV epoxy is optically polished. (FIG. 9(d)). The fiber and control wires are connected to an umbilical cord, and a handle is affixed to the stainless steel tube.

EXAMPLE 8

Manufacture of Blunt Probe

The construction of a blunt probe is illustrated schematically in FIGS. 10(a) through 10(d) (not to scale). A circular fixture is used to load the mirror assembly to a predetermined position within stainless steel tubing, slightly more than 1 mm inside diameter (FIG. 10(a)). The fixture includes a spring clip to position the mirror assembly against one side of the tube, and an open area to allow the passage of control wires and the fiber. The tube is of minimal length, and the fixture is epoxied to the inside of the tube, protruding by a few mm. A fiber attached to the GRIN lens is threaded through the stainless steel tubing, and through the open area in the mounting fixture, until the lens comes to a stop against the substrate of the mirror assembly. (FIG. 10(b)) A very small amount of epoxy is optionally placed on the fiber near the lens, and carried under the mirror assembly, bonding it to the stainless tube. UV-curing epoxy is added to the tube, covering the lens from the back side to the top of the tube (FIG. 10(c)). The tube is cut for a focal length of 1.57 mm past the distal end of the lens, and the cured UV epoxy is optically polished. The fiber and control wires are threaded through a polyimide tube of the same inner and outer diameter as the stainless steel tube. The polyimide tube is epoxied over the mounting fixture, flush with the stainless tube, and the wires and fiber are brought to a connector at the end. (FIG. 10(d)).

Figure 11:
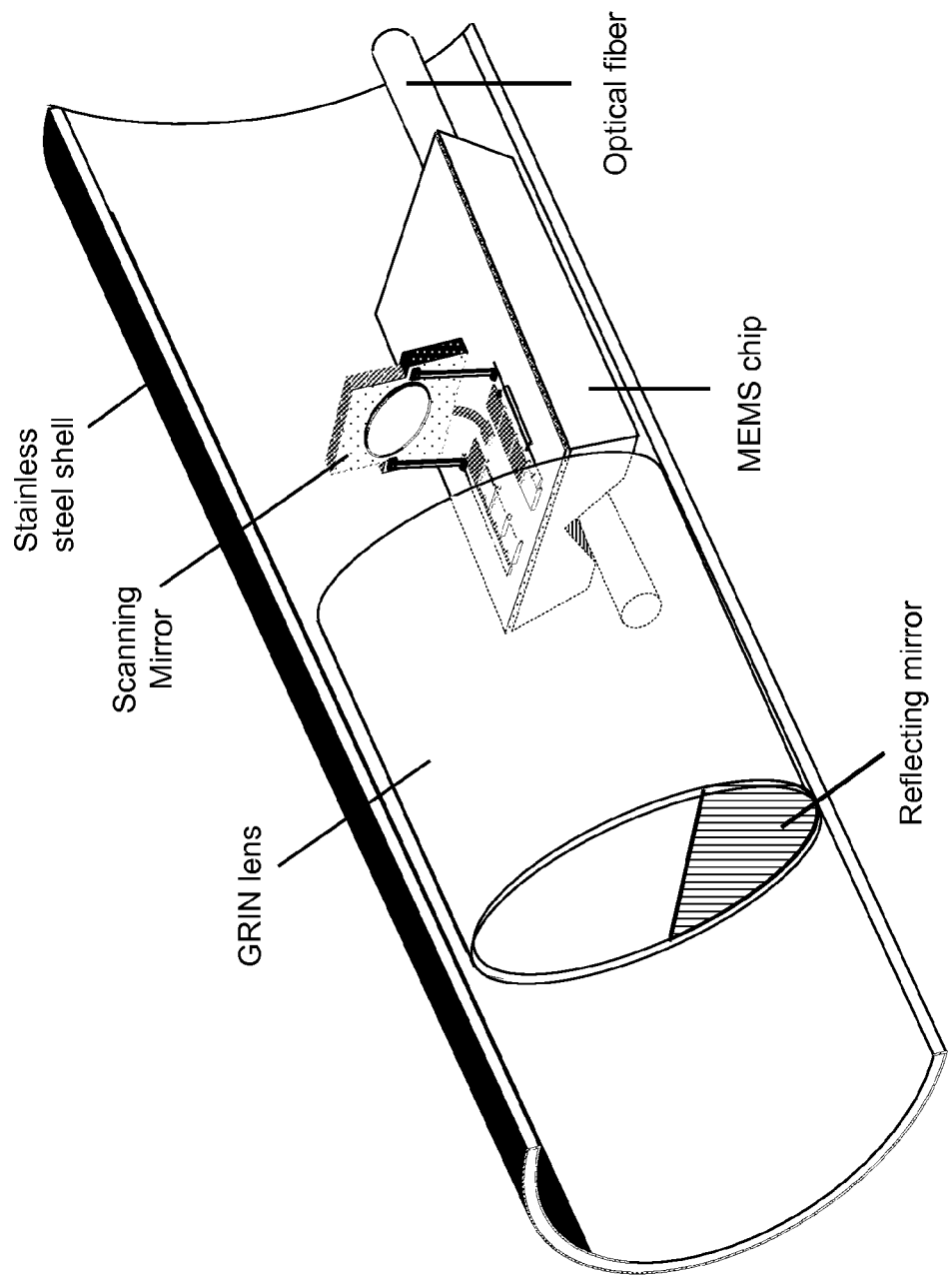
FIG. 11 depicts schematically some of the elements that are common to both rigid and flexible probes used in embodiments of this invention.

FIG. 11 depicts schematically some of the elements that are common to both sharp (generally rigid), and blunt (generally flexible) probes. For clarity, the spacing material and electrical wires are not shown.

EXAMPLE 9

The mechanical performance of the scanning mirror is confirmed for deflection range, response time, linearity, sensitivity, and repeatability. The performance of the optical system is confirmed for resolution, focal distance, flatness of field, and lens aberrations such as spherical aberration, coma, and distortion. The focused spot is projected onto a screen. Images are taken with a frame grabber, and are analyzed off-line. Preliminary tests are performed in visible laser light at 0.633 µm, followed by more extensive tests at the operating wavelength of 1.3 µm. As a final check, one-dimensional images of resolution test patterns are obtained.

EXAMPLE 10

Integration and Testing of the Endoscope in the OCT System

After assembly and preliminary testing of the mechanical and optical systems, endoscopes are integrated into an OCT system, as generally depicted schematically in FIG. 4. The prototype system to be used for the initial testing will be a modified, commercially-purchased, side-firing endoscopic OCT system, adapted with a prototype, forward-scanning endoscope in accordance with the present invention. The previous (side-firing) endoscope probe will be removed from the system, and replaced with the novel forward-scanning MEMS endoscope probe, optically connected to a 2×2 coupler. After measuring the length of the MEMS endoscope, a patch cable will be fabricated to match the optical path length of the reference arm, taking into consideration the airspace in the optical delay line. Minor optical path length adjustments can be made within the delay line as needed. The MEMS control line will be connected to the OCT system DAQ board output. OCT system software will supply a structured waveform to the MEMS scanner to produce a 0.7 mm beam sweep at up to 180 Hz. Signal acquisition software will synchronize with MEMS scanning.

After the system is fully assembled, a series of tests is conducted to assess endoscopic function and OCT image quality. Some tests will repeat the same tests previously described. Additional tests include the following:

1. Optical throughput: The ratio of the power from the distal end of the endoscope to the power from the fiber splitter is calculated to determine losses in the fiber coupler and endoscope. A preferred throughput is at least ~75%.
2. Axial resolution: The point spread function, or axial resolution, will be measured as the full-width at half-maximum of the reflection from a mirror. Axial resolution is primarily a function of the source; however it can also be negatively influenced by aberrations and spectral filtering characteristics of the endoscope itself. A preferred axial resolution sees no more than ~10% degradation of the resolution.
3. Focal distance: The distance from the distal tip of the endoscope to the focal plane will be measured by translating a mirror along the beam axis to find the location of the maximum signal. The focal distance is then calculated by subtracting the position of the distal tip reflection from the position of the mirror reflection, using A-scan data. These measurements are taken at the center and at both extremes of the scan range, to estimate focal plane curvature. A preferred focal distance is ~50-400 µm from the distal tip of the endoscope. A preferred field curvature is less than ~40 µm.
4. Lateral resolution and depth of focus: The spot size at several positions along the beam axis will be measured using the knife-edge technique, and the results will be fit to a Gaussian beam equation to estimate the focused spot size (taken as the lateral resolution) and the depth of focus. The preferred spot size is less than ~7 µm, and the preferred depth of focus should be not less than ~40 µm.
5. Scan range and scan linearity: An image of a slide with mirrored rulings at a pitch of 100 µm will be obtained for various endoscope-slide separation distances. The scan linearity and scan range as a function of distance will be plotted. A preferred scan range is greater than ~0.5 mm at focus. A preferred level of non-linearity is less than ~10%. Optionally, the structured waveform to the scanner may be altered to improve linearity.
6. System dynamic range: The dynamic range of the entire system (full range, mirror to noise) is measured using a technique that has previously been used for other endoscopic systems, because the insertion of a neutral density filter into the sample arm path can be impractical. First, the power output by the endoscope will be measured. Second, the standard deviation of the noise is measured with the endoscope immersed in water (i.e. with no sample reflections). Third, the fiber coupling to the endoscope is loosened, and the magnitude of this "attenuation" is calculated by measuring the new power output by the endoscope. The attenuations should be ~40-50 dB. Fourth, the interferometric signal strength with a mirror located at focus is measured. Finally, the system's dynamic range is calculated as $20*\log_{10}[\text{signal/SD noise}]+\text{attenuation}$. A preferred dynamic range for the system is greater than ~98 dB.
7. Ghosting artifacts: Strong reflections from distal endoscope components can cause unwanted "ghosting" artifacts, typically appearing at the top of images. Their possible presence will be assessed by imaging over the full lateral range of the endoscope while the endoscope is immersed in water. It is preferred that any "ghost" reflections have an intensity at least ~60 dB below the magnitude of a mirror reflection from the focal plane.
8. Image quality: images will be taken of objects commonly reported in the literature, e.g., onion, human fingertip, rodent skin. The quality of images will be compared (subjectively) with images previously reported with prior endoscope systems. A quantitative assessment of image dynamic range will also be performed. A preferred average image dynamic range for human fingertip is ~30 dB.

EXAMPLE 11

In Vivo Imaging in Rats

After these tasks are completed, a pilot imaging study will be conducted, in rat stomach. This study will demonstrate successful, in vivo, minimally invasive imaging in a clinically relevant organ, with difficult (small diameter) access. In subsequent studies and in clinical settings, the novel endoscope will be used for imaging other endoscopically accessible organ systems, including for example urogenital tissues, the respiratory tract, and musculoskeletal tissues, including joints. Additionally, we believe that the endoscope will be useful to facilitate and augment biopsy procedures in solid tissue, including mammary, ovarian, renal, and hepatic tissues.

The imaging protocol will be as follows:

1. Twelve Fischer 344 rats, approximately 150 g each, will be used for this study. This number will provide a good indication of the ease of endoscope insertion, the range of the stomach that can readily be imaged, and those features of the stomach that can easily be visualized. Statistical analyses may optionally be conducted.
2. Rats will be anesthetized with Avertin (15 mg/kg), administered i.p.
3. The OCT endoscope will be introduced through the mouth, down the esophagus, and into the stomach. OCT images will be obtained throughout the area accessible to the endoscope. We expect to collect images of the cardiac, body, and pyloric regions of the stomach in each rat.
4. Upon completion of the imaging procedures, animals will be euthanized by $CO_2$ asphyxiation.
5. To confirm the precise location of the endoscope within the stomach, and to determine the percentage of the stomach lining that can be imaged with this design, and to permit correlation of histological sections with OCT images, the endoscope will be re-introduced into the euthanized rat. An abdominal incision will be made and the stomach exposed. The position of the endoscope throughout its entire range of movement will be noted and the extremes marked on the outside of the stomach with tissue marking dye. A series of in situ OCT images will be obtained from the stomach cardia to pylorus in 1 mm increments. Measurements will be made of the width of the gastric wall and layers at each level.
6. The stomach will be excised and the area of the stomach imaged with OCT will be isolated and laid flat on filter paper. The tissue will be fixed with histochoice and embedded in paraffin. Transverse gastric wall sections will be prepared at levels corresponding to each of the in situ images, and stained with H&E.
7. Digital light photomicrographs of all sections will be taken at a magnification comparable to that used for the OCT images. Using software such as Image Pro, precise, calibrated, microscopic measurements and images will be taken of the width of the entire gastric wall and of each of the layers (mucosa, submucosa, muscularis mucosa, and muscularis externa) in each section. The percentage of the wall represented by each layer will be determined and compared to that in corresponding OCT images. Percentages are used rather than absolute measurements to compensate for possible tissue shrinkage during fixation.

8. The in vivo and in situ OCT images are compared to identify any substantial differences between the two. (For example, it is possible that the presence or absence of blood flow could have an influence.) The in situ OCT images will also be compared to histological sections. Quantitative measurements by regression analysis will compare the percentage of gastric wall represented by each of the layers in the OCT images and light photomicrographs.

The imaging study will be considered potentially useful for clinical applications if: 1) the endoscope is successfully introduced into the stomachs of all 12 rats, 2) at least one-half of the area of the gastric wall is successfully imaged, and 3) the ability to accurately measure the thickness of the mucosa, submucosa and total stomach wall thickness, as determined by comparison to histological sections, with a correlation between the two types of measurement better than 0.7.

These observations and measurements will confirm that the novel OCT system with its highly-miniaturized, forward-looking endoscope should have an in vivo image quality equaling that previously obtained only with larger forward-looking endoscopies, or with side-firing endoscopes.

Definitions. Certain directional terms are used in the specification and claims for convenience of reference. Unless the context clearly indicates otherwise, the following definitions will apply:

A part of a device or a part of a component that is positioned relatively closer to (or that is intended to be positioned relatively closer to) a tissue or other sample to be imaged may sometimes be referred to as "distal," and a part of a device or a part of a component that is relatively farther from the tissue or other sample may sometimes be referred to as "proximal." Likewise, one side of a device or one side of a component may sometimes be referred to as the "top," and the side of the device or the side of the component that is in the opposite direction from the "top" may sometimes be referred to as the "bottom." It is understood that the direction from distal-to-proximal is perpendicular to (or approximately perpendicular to) the direction from top-to-bottom. It is also understood that the directions "top" and "bottom" are used for convenience of reference, that they refer to a frame of reference that is defined with respect to a particular device or a component, and that the directions "top" and "bottom" do not necessarily coincide with directions that may be determined with respect to a local gravitational field. As an example, referring to the device depicted in FIG. 3, "distal" is to the right, "proximal" is to the left, "top" is up, and "bottom" is down. These same directional designations will apply regardless of the orientation of the device in space, and regardless of its orientation relative to the local gravitational field. Note that the "bottom" of a probe will often (but not necessarily) refer to the side of the probe where the optical fiber connects to the lens, and to the side of the probe containing the fixed mirror. Note also that the "top" will often (but not necessarily) refer to the side of the probe containing the scanning mirror. The directions "proximal," "distal," "top," and "bottom" should be used consistently for a particular device and all components of the same device. For example, once the "top" direction is defined for a particular device, then the "top" direction for all components of the same device will be the same as (or parallel to) the "top" direction for the device itself. Note that, consistent with these definitions, a "forward-looking" endoscopic probe is one that acquires images from a sample that is located in the direction that is distal to the distal end of the probe.

The complete disclosures of all references cited in this specification, including without limitation the complete disclosure of the priority application, are hereby incorporated by reference. Any Internet-accessible supplemental materials that were published or otherwise made publicly available in association with any of the cited references are included within this incorporation by reference. In the event of an otherwise irreconcilable conflict, however, the present specification shall control.

What is claimed:

1. A device adapted for use as a forward-looking, optical coherence endoscopic probe to collect images of a sample; wherein said device comprises a tube, a lens, an optical fiber, a fixed mirror, and a scanning mirror; wherein:
   (a) the interior of said tube is adapted to hold said lens, said optical fiber, said fixed mirror, and said scanning mirror;
   (b) said lens is affixed to the interior of said tube, at or near the distal end of said tube; and the index of refraction of said lens may be constant or may vary as a function of position within said lens;
   (c) said optical fiber is affixed to or near the bottom of the interior of said tube, or is affixed to or near the bottom of the proximal side of said lens, or both; and said optical fiber is optically coupled to said lens, at or near the bottom of the proximal side of said lens, wherein the orientation of said optical fiber is adapted to deliver light to the lens, so that light will travel from said fiber through the bottom of said lens in a direction approximately proximal-to-distal, towards said fixed mirror;
   (d) said fixed mirror is affixed to or near the bottom of the interior of said tube, or is affixed to or near the bottom of the distal side of said lens, or both, wherein the orientation and position of said fixed mirror are adapted to reflect light traveling from said fiber back through said lens, in a direction approximately distal-to-proximal, towards said scanning mirror;
   (e) said scanning mirror is affixed to or near the top of the interior of said tube, proximal to the proximal side of said lens; wherein the orientation and position of said scanning mirror are adapted to reflect light traveling from said fixed mirror back through said lens, in a direction approximately proximal-to-distal, towards the top of the distal side of said lens; and wherein said device additionally comprises an actuator to vary the orientation, position, or both of light reflected by said scanning mirror;
   (f) the size, index of refraction, and shape of said lens; and the positions and orientations of said optical fiber, said lens, said fixed mirror, and said scanning mirror are adapted to cause light from said optical fiber to traverse said lens three times: first, from said fiber through said lens in a direction approximately proximal-to-distal, to said fixed mirror; second, from said fixed mirror through said lens and exiting said lens in a direction approximately distal-to-proximal, to said scanning mirror; and third, from said scanning mirror to said lens, through said lens in a direction approximately proximal-to-distal, exiting said lens, and continuing to a focal plane that is coincident or approximately coincident with the sample or a portion of the sample; wherein the refraction of the light during the three passes through the lens brings the light to a focus or to an approximate focus at the focal plane; and (g) said device is adapted also to collect and focus light that is thereby backscattered from the sample in the focal plane, in the reverse direction from the direction of the incident light: first, from the focal plane to said lens and through said lens to said scanning mirror in a direction approximately distal-to-proximal; second, from said scanning mirror through said lens to said fixed mirror in a direction approximately proximal-to-distal; and third, from said fixed mirror through said lens to said fiber in a direction approximately distal-to-proximal, and coming to a focus or to an approximate focus at the distal end of said fiber; whereby said fiber collects light scattered by the sample.

2. A device as recited in claim 1, wherein said lens comprises a graded index lens having a right circular cylindrical shape, wherein the refractive index of said graded index lens varies as a function of the distance from the cylindrical axis.

3. A device as recited in claim 1, additionally comprising a broadband light source for emitting near-infrared radiation having a coherence length between about 5 µm and about 20 µm; a reference arm; a beam splitter adapted to direct a portion of the infrared radiation to the reference arm and a portion to the fiber; a mixer; and a detector; wherein:

(a) the mixer is adapted to optically combine light output by the reference arm and light output from said fiber after back-scattering from a sample, to produce an interference pattern, and to output the interference pattern to said detector;

(b) the optical path length from said splitter to the focal plane of said lens and back to said mixer, and the optical path length from said splitter through said reference arm and to said mixer, are equal to one another to within a distance that is not more than about the coherence length.

4. A device as recited in claim 3, wherein said device is adapted to collect images from different depths within the sample by varying the optical path length of said reference arm, or by varying the position of the distal end of said lens, or both.

5. A device as recited in claim 1, wherein said tube is rigid; wherein said device additionally comprises a spacer within said tube, distal to said lens; wherein said spacer is transparent to near-infrared radiation; and wherein the distal end of said spacer is blunt.

6. A device as recited in claim 1, wherein at least a portion of said tube is flexible; wherein said device additionally comprises a spacer within said tube, distal to said lens; wherein said spacer is transparent to near-infrared radiation; and wherein the distal end of said spacer is pointed and is adapted to penetrate tissue.

7. A device as recited in claim 1, wherein the outer diameter of said tube is 1.5 mm or smaller.

8. A device as recited in claim 1, wherein said scanning mirror is adapted to scan in two, non-parallel directions.

* * * * *